(12) United States Patent
Xu et al.

(10) Patent No.: US 11,358,945 B2
(45) Date of Patent: Jun. 14, 2022

(54) METHOD FOR PREPARING CYCLOPENTA[C]CHROMIUM COMPOUND

(71) Applicant: SOOCHOW UNIVERSITY, Suzhou (CN)

(72) Inventors: Fan Xu, Suzhou (CN); Dandan Li, Suzhou (CN); Xiaoyou Ding, Suzhou (CN); Yanan Zhu, Suzhou (CN); Zhigang Yao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 41 days.

(21) Appl. No.: 17/163,480

(22) Filed: Jan. 31, 2021

(65) Prior Publication Data

US 2021/0147377 A1 May 20, 2021

Related U.S. Application Data

(63) Continuation of application No. PCT/CN2018/097757, filed on Jul. 30, 2018.

(51) Int. Cl.
*C07D 311/94* (2006.01)
*B01J 31/02* (2006.01)

(52) U.S. Cl.
CPC .......... *C07D 311/94* (2013.01); *B01J 31/0252* (2013.01)

(58) Field of Classification Search
CPC .................................................. C07D 311/94
USPC ............................................................ 514/454
See application file for complete search history.

(56) References Cited

FOREIGN PATENT DOCUMENTS

CN    108774207 A    11/2018

OTHER PUBLICATIONS

Wang et al., "Iron-Mediated [3+2] or [3+3] Annulation of 2-(2-(Ethynyl)phenoxy)-1-arylethanones: Selective Synthesis of Indeno[1,2-c]chromenes and 5H-Naphtho[1,2-c]chromenes" Organic Letters, 2011 vol. 13, No. 1, 14-17 Jan. 12, 2010).
Luo et al., "Efficient generation of indeno[1,2-c]chromenes via the Pd-catalyzed reaction of 2-alkynylhalobenzenes with 2-alkynylphenols" Chem. Commun., 2011, 47, 5298-5300 (Mar. 31, 2011).

*Primary Examiner* — Taofiq A Solola
(74) *Attorney, Agent, or Firm* — SZDC Law P.C.

(57) ABSTRACT

The present invention discloses a method for preparing a cyclopenta[c]chromene compound. A cationic rare earth compound $[Ln(CH_3CN)_9]^{3+}[(AlCl_4)_3]^{3-}\cdot CH_3CN$ is used as a catalyst, and p-methyl thiophenol is used as an accelerator for a catalytic reaction of a chalcone compound so as to prepare a product; and Ln, contained in the catalyst, represents a positive trivalent rare earth metal ion and is selected from one of La, Nd, Sm, Gd and Yb. According to the method, the starting materials are easy to obtain, the reaction process is simple, the catalyst usage is low, the catalyst is universally applicable to various substituted 2-hydroxy chalcones, and the obtained cyclopenta[c]chromene compound has not been reported. The catalyst synthesis method is simple and easy to obtain, and the yield of the target product is high.

7 Claims, No Drawings

METHOD FOR PREPARING CYCLOPENTA[C]CHROMIUM COMPOUND

This application is a Continuation Application of PCT/CN2018/097757, filed on Jul. 30, 2018, which is incorporated by reference for all purposes as if fully set forth herein.

TECHNICAL FIELD

The invention relates to the technical field of preparation of organic oxo fused ring compounds, and particularly a method for preparing cyclopenta[c]chromene compounds.

BACKGROUND TECHNIQUE

Cyclopenta[c]chromene is an important class of oxa-fused ring compounds. Most of the compounds containing cyclopenta[c]chromene structure have good biological activity. At the same time, cyclopenta[c]chromene is also an important precursor compound that synthesizes many biologically active natural products (such as 11-oxasteroid compounds). Therefore, developing an effective method for synthesizing the cyclopenta[c]chromene skeleton has important theoretical and practical significance.

In the conventional art, the synthetic routes of the cyclopenta[c]chromene skeleton have been reported to be relatively limited. The main routes used are: Cycloaddition reaction of 6-dimethylaminofulvene and benzoquinone. (Hong, B.; Chen, Z.; Chen, W. Org. Lett. 2000, 17, 2647); palladium-catalyzed reaction of haloalkyne and 2-alkynylphenol (Luo, Y.; Hong, L.; Wu, J. Chem. Commun. 2011, 47, 5298).

Technical Problem

The common feature of these synthetic routes is that the required substrates are relatively complicated, mostly involving aryl mono- and di-yne compounds, and often require the participation of precious metals or metered bases, and the yields are mostly low, so they have certain limitations. It is particularly outstanding that in these methods, cyclo-penta[c]chromene compounds are only available individually, and most of the synthetic methods finally obtain indeno[c]chromene compounds, so the research on the synthesis of the former is very Lack.

Technical Solutions

In view of the good biological activity of the cyclopenta[c]chromene skeleton compounds, a simple, high-activity, and universally catalytic method for the synthesis of cyclopenta[c]chromene compound is necessary.

The object of the present invention is to provide a cyclopenta[c]chromene compound and a preparation method thereof. The reaction of a chalcone compound catalyzed by a cationic rare earth compound is disclosed which is a suitable method for synthesizing cyclopenta[c]chromene compounds.

In order to achieve the above-mentioned object of the invention, the technical solution adopted by the present invention is:

A method for preparing a cyclopenta[c]chromene compound includes the following steps: under anhydrous and anaerobic conditions, using a chalcone compound as a reactant, using a cationic rare earth compound as a catalyst, and p-methyl thiophenol is a promoter, and reacting to obtain the cyclopenta[c]chromene compound.

The chemical structural formula of the cationic rare earth compound is as follows:

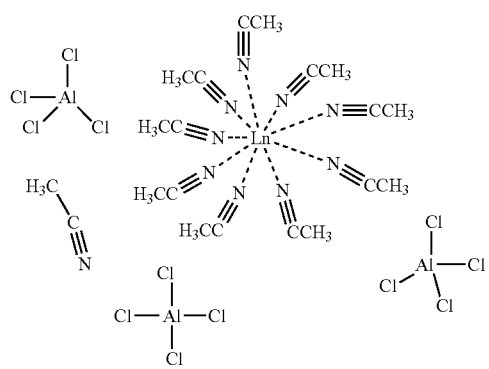

Wherein Ln is selected from the group consisting of La, Nd, Sm, Gd, and Yb.

The general chemical structure of the chalcone compound is as follows:

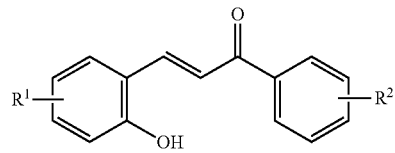

Wherein, $R^1$ is selected from the group consisting of hydrogen, 3-chloro, 4-chloro, 4-methoxy, 5-chloro, 5-bromo, 5-methyl, 5-methoxy, and 6-chloro; $R^2$ is selected from the group consisting of hydrogen, 3'-chloro, 3'-bromo, 3'-methoxy, 4'-chloro, 4'-bromo, 4'-phenyl, and 4'-methoxy.

In the above technical solution, the anhydrous and oxygen-free conditions are preferably an inert atmosphere.

In the above technical scheme, the reaction is performed in an organic solvent, the organic solvent is selected from the group consisting of chlorobenzene, acetonitrile, dichloroethane, and toluene, preferably chlorobenzene. Under the same conditions, the reaction yield in chlorobenzene much higher than other solvents.

In the above technical solution, the general formula of the catalyst cationic rare earth compound is: $[Ln(CH_3CN)_9]^{3+}[(AlCl_4)_3]^{3-} \cdot CH_3CN$; wherein Ln represents a positive trivalent rare earth metal ion, selected from the group consisting of lanthanum, neodymium, samarium, gadolinium or ytterbium, preferably ytterbium. Under the same conditions, compared to the other four metals, the reaction catalyzed by ytterbium catalyst has a higher yield for the formation of cyclopenta[c]chromene.

In the above technical solution, the amount of the catalyst used is 1 to 8%, preferably 2 to 5%, and more preferably 3%, of the moles of the chalcone compound. The reaction can be performed efficiently and the reaction cost is low.

In the above technical solution, the amount of p-methyl thiophenol is 0.6 to 1.3 times, preferably 1.1 to 1.2, and more preferably 1.2 times, of the moles of the chalcone compound. The reaction cannot be performed efficiently, but too large an amount will cause waste and complicate the post-treatment of the reaction system.

In the above technical solution, the reaction temperature is 80 to 140° C., preferably the reflux temperature of the organic solvent, and more preferably the reflux temperature of chlorobenzene; and the reaction time is 24 to 72 hours, preferably 36 hours.

The invention also discloses the application of a cationic rare earth compound and p-methyl thiophenol in the preparation of a cyclopenta[c]chromene compound, or the application of a chalcone compound in the preparation of a cyclopentadiene [c] chromene compound. In the application, a cationic rare earth compound is preferably used as a catalyst. In the presence of p-methyl thiophenol, a chalcone compound is used in the preparation of a cyclopenta[c] chromene compound.

The invention also discloses the application of p-methyl thiophenol as a promoter in the preparation of a cyclopentadien [c] chromene compound in the presence of a cationic rare earth compound.

In the present invention, the chemical structure of the product cyclopenta[c]chromene compound is as follows:

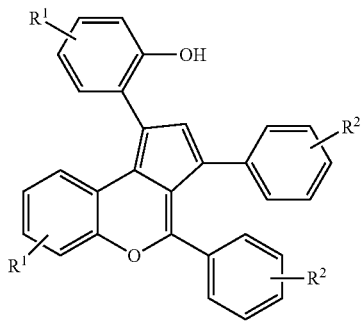

In the above technical solution, the reaction process includes mix chalcones, cationic rare earth compounds [Ln(CH$_3$CN)$_9$]$^{3+}$[(AlCl$_4$)$_3$]$^{3-}$.CH$_3$CN and a small amount of solvent and stir for a few minutes, then add p-methyl thiophenol and a small amount of solvent, mix well, stir at 80 to 140° C. for 24 to 72 hours, stop the reaction, perform extraction, dry the extract with a desiccant, filter, and reduce The solvent was removed under pressure, and finally cyclopenta[c]chromene compound was obtained by silica gel flash column chromatography.

In the above technical solution, operations, such as quenched the reaction, extracting, removing the solvent under reduced pressure, and finally obtaining cyclopenta[c] chromene by silica gel flash column chromatography, are known to one of ordinary skill. The extraction agent used therein, drying agents and eluents are also known, and those skilled in the art can select appropriate agents according to the properties of the final product. In a preferred technical solution, the reaction is quenched with water, the exctaction agent is ethyl acetate, the drying agent is anhydrous sodium sulfate, and the eluent is ethyl acetate/petroleum ether system (volume ratio is 1:20 to 1:15).

The above technical solution can be expressed as follows:

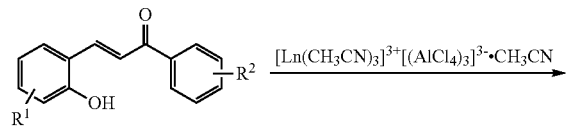

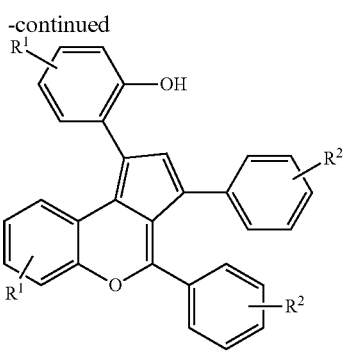

Beneficial Effect

1. The present invention uses the cationic rare earth compound [Ln(CH$_3$CN)$_9$]$^{3+}$[(AlCl$_4$)$_3$]$^{3-}$.CH$_3$CN as catalyst for the first time to catalyze the reaction of chalcone compounds to prepare cyclopenta[c]chromene compounds, and the starting materials are easy to obtain. The reaction process is simple, and the yield of the target product is high, up to 70%;
2. The method disclosed by the invention uses a small amount of catalyst, post-treatment of the reaction is simple, and the product is easy to be purified;
3. The catalyst disclosed in the present invention is universal to a variety of substituted chalcone compounds, and the obtained cyclopenta[c]chromene compounds have not been reported;
4. The catalytic synthesis method used in the invention is simple and easy to operate;
5. The method disclosed in the present invention does not use a noble metal catalyst and does not use a strong base, the reaction cost is low, and the reaction is environmental friendly.

EMBODIMENTS OF THE INVENTION

EXAMPLE 1

Synthesis of catalyst [Yb(CH$_3$CN)$_9$]$^{3+}$[(AlCl$_4$)$_3$]$^{3-}$.CH$_3$CN

Under the protection of argon, 0.70 g (2.5 mmol) of YbCl$_3$ and 1.00 g (7.5 mmol) of anhydrous AlCl$_3$ were added into a dehydrated and deoxidized reaction flask in a molar ratio is 1:3, 25 mL of acetonitrile was added to dissolve reactants. Centrifugal treatment was carried out after stirring for 24 hours at room temperature, taking the supernatant, concentrating and leaving it in a refrigerator at 0° C. to obtain crystalline [Yb(CH$_3$CN)$_9$]$^{3+}$[(AlCl$_4$)$_3$]$^{3-}$.CH$_3$CN, a yield of 46%.

Other [Ln(CH$_3$CN)$_9$]$^{3+}$[(AlCl$_4$)$_3$]$^{3-}$.CH$_3$CN catalysts could be prepared using the same method of Example 1, with different rare earth chlorides.

EXAMPLE 2

[Yb(CH$_3$CN)$_9$]$^{3+}$[(AlCl$_4$)$_3$]$^{3-}$.CH$_3$CN catalyzed reaction of 2-hydroxy-chalcone to prepare cyclopenta[c]chromene compound

[Yb(CH$_3$CN)$_9$]$^{3+}$[(AlCl$_4$)$_3$]$^{3-}$.CH$_3$CN(0.0163 g, 0.015 mmol, 3 mol %), 2-hydroxy-chalcone (0.1121 g, 0.5 mmol) and chlorobenzene (1 mL) were added into a dehydrated and deoxidized reaction flask, stirred for 2 minutes. p-Methyl thiophenol (0.0745 g, 0.6 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running a flash column chromatography on a silica gel column (Eluent: $V_{ethyl\ acetate}$:$V_{petroleum\ ether}$ is 1:20 to 1:15) to obtain a red-brown solid. The solid was placed under an oil pump and continued to be dried for about one day. The yield was 70%. When the accelerator was changed to 2% or 5%, the yield was 65% or 71%, respectively. When the solvent was changed to acetonitrile or toluene, the yield was 45% or 46%, respectively. When the solvent was changed to DMF, the reaction cannot proceed. When the reaction was changed to 100 ° C., the yield was 52%. When the catalyst was changed to "3% $YbCl_3$ +9% $AlCl_3$," the yield was 25%. When the catalyst was changed 3% $YbCl_3$, the yield was 20%. When the accelerator was changed to 1-mercaptodecane, the yield was 24%.

The theoretical molecular formula and NMR spectrum of the product are shown below. It can be seen from the analysis that the actual synthesized product is consistent with the theoretical analysis.

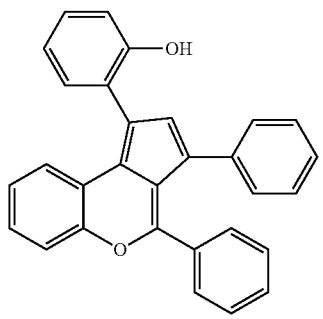 [SMILES: Oc1ccccc1-c1cc(-c2ccccc2)c2c(-c3ccccc3)oc3ccccc3c1-2]

$^1$H NMR (400 MHz, $CDCl_3$) δ 7.70 (d, J=8.0 Hz, 1H), 7.60 (d, J=8.4 Hz, 1H), 7.47-7.44 (m, 3H), 7.37-7.28 (m, 3H), 7.24-7.20 (m, 1H), 7.16-7.13 (m, 2H), 7.11-7.04 (m, 3H), 7.02-6.96 (m, 5H), 5.42 (s, 1H).

EXAMPLE 3

$[La(CH_3CN)9]^{3+}[(AlCl_4)_3]^{3-} \cdot CH_3CN$ catalyzed reaction of 2-hydroxy-chalcone to prepare cyclopenta[c]chromene compound $[La(CH_3CN)9]^{3+}[(AlCl_4)_3]^{3-} \cdot CH_3CN$ (0.0158 g, 0.015 mmol, 3 mol %), 2-hydroxy-chalcone (0.1121 g, 0.5 mmol) and chlorobenzene (1 mL) were added into a dehydrated and deoxidized reaction flask, and stirred for 2 minutes. p-Methyl thiophenol (0.0745 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: $V_{ethyl\ acetate}$:$V_{petroleum\ ether}$ is 1:20 to 1:15) to obtain a red-brown solid. The solid was placed under an oil pump and continued to be dried for about one day. The yield was 62%.

EXAMPLE 4

$[Nd(CH_3CN)_9]^{3+}[(AlCl_4)_3]^{3-} \cdot CH_3CN$ catalyzed reaction of 2-hydroxy-chalcone to prepare cyclopenta[c]chromene compound $[Nd(CH_3CN)_9]^{3+}[(AlCl_4)_3]^{3-} \cdot CH_3CN$ (0.0159 g, 0.015 mmol, 3 mol %), 2-hydroxy-chalcone (0.1121 g, 0.5 mmol) and chlorobenzene (1 mL) were added into a dehydrated and deoxidized reaction flask, and stirred for 2 minutes. p-Methyl thiophenol (0.0745 g, 0.6 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: $V_{ethyl\ acetate}$:$V_{petroleum\ ether}$ is 1:20 to 1:15) to obtain a red-brown solid. The solid was placed under an oil pump and continued to be dried for about one day. The yield was 63%.

EXAMPLE 5

$[Sm(CH_3CN)_9]^{3+}[(AlCl_4)_3]^{3-} \cdot CH_3CN$ catalyzed reaction of 2-hydroxy-chalcone to prepare cyclopenta[c]chromene compound $[Sm(CH_3CN)_9]^{3+}[(AlCl_4)_3]^{3-} \cdot CH_3CN$ (0.0160 g, 0.015 mmol, 3 mol %), 2-hydroxy-chalcone (0.1121 g, 0.5 mmol) and chlorobenzene (1 mL) were added into a dehydrated and deoxidized reaction flask, and stirred for 2 minutes. p-Methyl thiophenol (0.0745 g, 0.6 mmol) and chlorobenzene (1 mL) were added, and stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: $V_{ethyl\ acetate}$:$V_{petroleum\ ether}$ is 1:20 to 1:15) to obtain a red-brown solid. The solid was placed under an oil pump and continued to be dried for about one day. The yield was 63%.

EXAMPLE 6

$[Gd(CH_3CN)_9]^{3+}[(AlCl_4)_3]^{3-} \cdot CH_3CN$ catalyzed reaction of 2-hydroxy-chalcone to prepare cyclopenta[c]chromene compound $[Gd(CH_3CN)_9]^{3+}[(AlCl_4)_3]^{3-} \cdot CH_3CN$ (0.0161 g, 0.015 mmol, 3 mol %), 2-hydroxy-chalcone (0.1121 g, 0.5 mmol) and chlorobenzene (1 mL) were added into a dehydrated and deoxidized reaction flask, and stirred for 2 minutes. p-Methyl thiophenol (0.0745 g, 0.6 mmol) and chlorobenzene (1 mL) were added, and stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: $V_{ethyl\ acetate}$:$V_{petroleum\ ether}$ is 1:20 to 1:15) to obtain a red-brown solid. The solid was placed under an oil pump and continued to be dried for about one day. The yield was 60%.

EXAMPLE 7

$[Yb(CH_3CN)_9]^{3+}[(AlCl_4)_3]^{3-} \cdot CH_3CN$ catalyzed reaction of 3-(4-chloro-2-hydroxyphenyl)-1-phenyl-2-propen-1-one to prepare cyclopenta[c]chromene compound $[Yb(CH_3CN)_9]^{3+}[(AlCl_4)_3]^{3-} \cdot CH_3CN$ (0.0273 g, 0.025 mmol, 3 mol %), 3-(4-chloro-2-hydroxyphenyl)-1-phenyl- 2-propen-1-one (0.1293 g, 0.5 mmol) and chloro-benzene (1 mL) were added into a dehydrated and deoxidized reaction flask, and stirred for 2 minutes. p-Methyl thiophenol (0.0745 g, 0.6 mmol) and chlorobenzene (1 mL) were added, and stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: $V_{ethyl\ acetate}$:$V_{petroleum\ ether}$ is 1:20 to 1:15) to obtain a red-brown solid. The solid was placed under an oil pump and continued to be dried for about one day. The yield was 69%. When p-methyl thiophenol was changed to 2-naphthol (0.0961 g, 0.6 mmol), the yield was 55%.

The theoretical molecular formula and NMR spectrum of the product are shown below. It can be seen from the analysis that the actual synthesized product is consistent with the theoretical analysis.

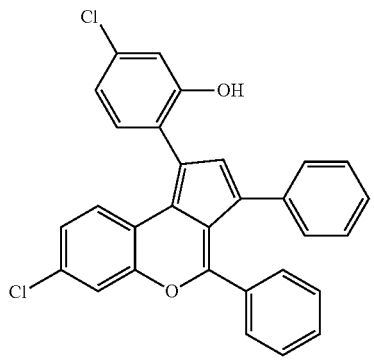 [SMILES: Oc1cc(Cl)ccc1-c1cc(-c2ccccc2)c2c(-c3ccccc3)oc3cc(Cl)ccc3c1-2]

$^1$H NMR (400 MHz, CDCl$_3$) δ 7.62 (d, J=2.0 Hz, 1H), 7.57(d, J=8.8 Hz, 1H), 7.44-7.42 (m, 2H), 7.35-7.30 (m, 2H), 7.21 (dd, J=8.8, 2.0 Hz, 1H), 7.17-7.13 (m, 2H), 7.11 (d, J=2.0 Hz, 1H), 7.05-6.96 (m, 7H), 5.44 (s, 1H).

EXAMPLE 8

[Yb(CH$_3$CN)$_9$]$^{3+}$[(AlCl$_4$)$_3$]$^{3-}$·CH$_3$CN catalyzed reaction of 3-(2-hydroxy-4-methoxyphenyl)-1-phenyl-2-propene-1-ketone to prepare cyclopenta[c]chrom-ene compound

[Yb(CH$_3$CN)$_9$]$^{3+}$[(AlCl$_4$)$_3$]$^{3-}$·CH$_3$CN(0.0381 g, 0.035 mmol, 3 mol %), 3-(2-hydroxy-4-methoxyphenyl)-1-phenyl-2-propene-1-ketone (0.1272 g, 0.5 mmol) and chlorobenzene (1 mL) were added into a dehydrated and deoxidized reaction flask, and stirred for a few minutes. p-Methyl thiophenol (0.0745 g, 0.6 mmol) and chlorobenzene (1 mL) were added, and stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: $V_{ethyl\ acetate}$:$V_{petroleum\ ether}$ is 1:20 to 1:15) to obtain a red-brown solid. The solid was placed under an oil pump and continued to be dried for about one day. The yield was 62%. When p-methyl thiophenol was changed to 2-naphthol (0.0961 g, 0.6 mmol), the yield was 29%.

The theoretical molecular formula and NMR spectrum of the product are shown below. It can be seen from the analysis that the actual synthesized product is consistent with the theoretical analysis.

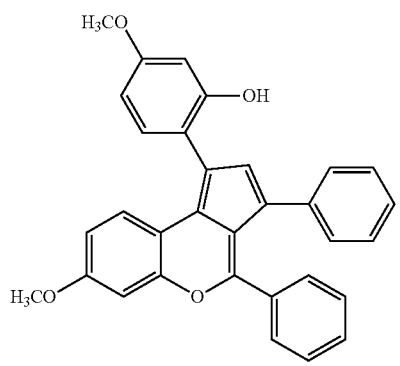 [SMILES: COc1ccc(-c2cc(-c3ccccc3)c3c(-c4ccccc4)oc4cc(OC)ccc4c2-3)c(O)c1]

$^1$H NMR (400 MHz, CDCl$_3$) δ 7.63 (d, J=9.2 Hz, 1H), 7.46-7.44 (m, 2H), 7.35-7.28 (m, 2H), 7.17-7.13 (m, 2H), 7.09 (d, J=2.8 Hz, 1H), 7.01-6.97 (m, 6H), 6.88 (dd, J=8.8, 2.8 Hz, 1H), 6.68 (d, J=2.4 Hz, 1H), 6.64 (dd, J=8.4, 2.8 Hz, 1H), 5.45 (s, 1H), 3.88 (s, 3H), 3.86 (s, 3H).

The invention claimed is:

1. A method for preparing a cyclopenta[c]chromene compound, comprising the following steps: under anhydrous and anaerobic conditions, using a chalcone compound as a reactant, using a cationic rare earth compound as a catalyst, using p-methyl thiophenol as an accelerator, and reacting in an organic solvent to prepare the cyclopenta[c]chromene compound, wherein the cationic rare earth compound has the following chemical structure:

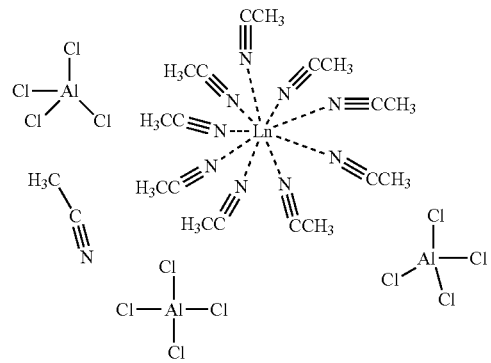

wherein, Ln represents a positive trivalent rare earth metal ion;

the chalcone compound has the following chemical structure:

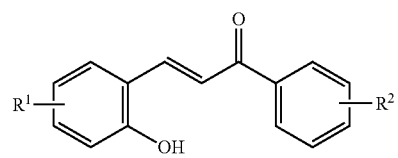

wherein, R$^1$ is selected from the group consisting of hydrogen, 3-chloro, 4-chloro, 4-methoxy, 5-chloro, 5-bromo, 5-methyl, 5-methoxy, and 6-chloro; R$^2$ is selected from the group consisting of hydrogen, 3'-chloro, 3'-bromo, 3'-methoxy, 4'-chloro, 4'-bromo, 4'-phenyl, and 4'-methoxy.

2. The method for preparing the cyclopenta[c]chromene compound according to claim 1, wherein the organic solvent is selected from the group consisting of chlorobenzene, acetonitrile, dichloroethane, and toluene; Ln is selected from the group consisting of La, Nd, Sm, Gd, and Yb; the anhydrous and oxygen-free conditions are inert atmosphere conditions.

3. The method for preparing the cyclopenta[c]chromene compound according to claim 2, wherein the organic solvent is chlorobenzene and the Ln is Ytterbium.

4. The method for preparing the cyclopenta[c]chromene compound according to claim 1, wherein a molar ratio of the catalyst:the chalcone compound:the accelerator is (0.01 to 0.08):1:(0.6 to 1.3).

5. The method for preparing the cyclopenta[c]chromene compound according to claim 4, wherein the molar ratio of the catalyst:the chalcone compound:the accelerator is (0.02 to 0.05):1:(1.1 to 1.2).

6. The method for preparing a cyclopenta[c]chromene compound according to claim 1, wherein a reaction temperature is 80 to 140 ° C.; and a reaction time is 24 to 72 hours.

7. The method for preparing the cyclopenta[c]chromene compound according to claim 6, wherein the reaction temperature is a reflux temperature of the organic solvent, and the reaction time is 36 hours.

\* \* \* \* \*